US00PP19833P2

(12) United States Plant Patent
Korlipara

(10) Patent No.: US PP19,833 P2
(45) Date of Patent: Mar. 17, 2009

(54) ***STOKESIA* PLANT NAMED 'PURPLE PIXIE'**

(50) Latin Name: *Stokesia laevis*
Varietal Denomination: Purple Pixie

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 11/999,759

(22) Filed: Dec. 6, 2007

(51) Int. Cl.
*A01H 5/00* (2006.01)

(52) U.S. Cl. ..... Plt./484

(58) Field of Classification Search ..... Plt./484
See application file for complete search history.

*Primary Examiner*—Kent L Bell
(74) *Attorney, Agent, or Firm*—Klarquist Sparkman, LLP

(57) ABSTRACT

A new and distinct *Stokesia* plant named 'Purple Pixie' characterized by a short, compact habit that doesn't open up with maturity, large violet blue flowers, and good vigor.

1 Drawing Sheet

Botanical denomination: *Stokesia laevis.*
Variety designation: 'Purple Pixie'.

The present invention relates to a new and distinct cultivar of *Stokesia* plant, botanically known as *Stokesia laevis,* and hereinafter referred to by the cultivar name 'Purple Pixie'. *Stokesia* is in the family Asteraceae. This new cultivar originated as a seedling from an open pollinated cross between *Stokesia laevis* 'Purple Parasols' (U.S. Plant Pat. No. 10,660), as the seed parent and an unknown *Stokesia laevis,* as the pollen parent.

Compared to *Stokesia* 'Purple Parasols' (U.S. Plant Pat. No. 10,660), *Stokesia* 'Purple Pixie' has shorter flowering stems and an upright habit rather than an open habit. It is a more compact version.

*Stokesia* 'Purple Pixie' is distinguished by:

1. a short, compact habit that doesn't open up with maturity,
2. large violet blue flowers,
3. good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in greenhouses and laboratories in Canby, Oreg., shows that the foregoing characteristics and distinctions come true to form and are established and transmitted through succeeding asexual propagations. The present plant has not been evaluated under all possible environmental conditions. The phenotype may vary with variations in environment without a change in the genotype of the plant.

BRIEF DESCRIPTION OF THE DRAWING

The photograph shows a 1 year old 'Purple Pixie' growing in the ground in full sun in the field in mid-summer in Canby, Oreg.

DETAILED PLANT DESCRIPTION

The following is a detailed description of the new *Stokesia laevis* cultivar based on observations of a 1-year-old specimen growing in the ground in full sun under typical outdoor conditions in Canby, Oreg. Canby is in Zone 8 on the USDA Hardiness map. Temperatures range from a high of 95 degrees F in August to an average of 32 degrees F in January. Normal rainfall in Canby is 42.8 inches per year in the trial fields in Canby, Oreg. The color descriptions are all based on the Royal Horticultural Society Colour Chart.

Plant:
- *Type.*—Herbaceous perennial.
- *Hardiness.*—USDA Zones 5 to 9.
- *Size.*—35 cm wide and 24 cm tall to top of flowers.
- *Form.*—Basal clump.
- *Vigor.*—Excellent.

Stem: acaulescent.

Leaf:
- *Type.*—Simple.
- *Shape.*—Lanceolate to oblong lanceolate.
- *Arrangement.*—Alternate and basal.
- *Blade size.*—Grows to 14.5 cm long and 2 cm wide.
- *Margins.*—Entire.
- *Apex.*—Acute.
- *Base.*—Attenuate.
- *Petiole description.*—Distal leaves sessile, proximal leaves petiolate and grow to 5 cm long and 1.5 mm wide, Green 138C, bases clasping.
- *Surface texture.*—Sparsely tomentose on both sides.
- *Venation.*—Pinnate.
- *Color.*—Topside — Green 137A with the vein Yellow Green 145C. Bottom side — Green 137C with the veins Green 138C.

Inflorescence:
- *Type.*—Corymbs.
- *Number of corymbs per plant.*—About 38, unbranched to 5-branched.
- *Peduncle description.*—Ascending, grows to 21 cm tall to terminal flower and 2.5 mm wide, internodes grow to 4.3 cm long, unevenly tomentose, Yellow Green 147B with small Brown 200A oval spots and scattered tomentum, White 155D.
- *Pedicel description.*—2.5 cm to 9 cm tall, grows to 1.8 mm in diameter, tomentose, Yellow Green 147B tinted with Brown 200A.

*Immature heads.*—While still developing the disc florets are tightly closed in a flat-topped ovoid, 44 mm wide and 12 mm deep, surrounded by the 4 layers of showy green phyllaries, Green 137A.

*Mature heads.*—6 cm wide and 3.3 cm deep, pseudo-radiant (corollas of peripheral, bisexual florets enlarged, zygomorphic).

*Phyllaries.*—About 35, in five leafy series, lanceolate, acuminate, margins pectinately spinose at the base, grows to 4 mm wide and 25 mm long, Green 137A on both sides.

*Ray florets.*—None.

*Disc florets.*—Perfect. Size— 2 cm to 3.7 cm wide and becoming 3.5 cm deep with maturity. Count — approximately 60 disc florets per inflorescence. Corolla — funnel form, tubes longer than throats, peripheral corollas enlarged and zygomorphic, grow to 4.2 cm long and 7 mm wide at the lobes, inner corollas more or less actinomorphic 2 cm to 3 cm long and 4 mm wide, 5 lobed, lobes lance-linear, corollas inside and out glabrous and colored Violet Blue 89C above the tube, with the tube Violet Blue 91C. Pistil — 1 per floret, 24 mm long; ovary White 155D and 3 mm long, 1 mm wide; style 20 mm long White 155A; stigma extruding, 2-branched, spreading 6 mm wide, White 155A. Stamen — 5 per floret, filaments 10 mm long and threadlike, White 155D, anthers flat and oblong shaped, 2.5 mm long, pollen Yellow 11B.

*Bloom period.*—July through September in Canby, Oreg.

*Lastingness.*—Each head lasts for about one week.

*Fragrance.*—None.

Seed: Not seen.

Disease and pests: *Stokesia* are susceptible to leaf spot and caterpillars. None of these have been observed on plants grown under commercial conditions in Canby, Oreg. No resistance is known.

COMPARISONS TO SIMILAR *Stokesia*

Compared to *Stokesia laevis* 'Purple Parasols' (U.S. Plant Pat. No. 10,660), 'Purple Pixie' has shorter flowering stems and an upright habit rather than an open habit. It is a more compact version.

I claim:

1. A new and distinct *Stokesia* plant named 'Purple Pixie' as herein illustrated and described.

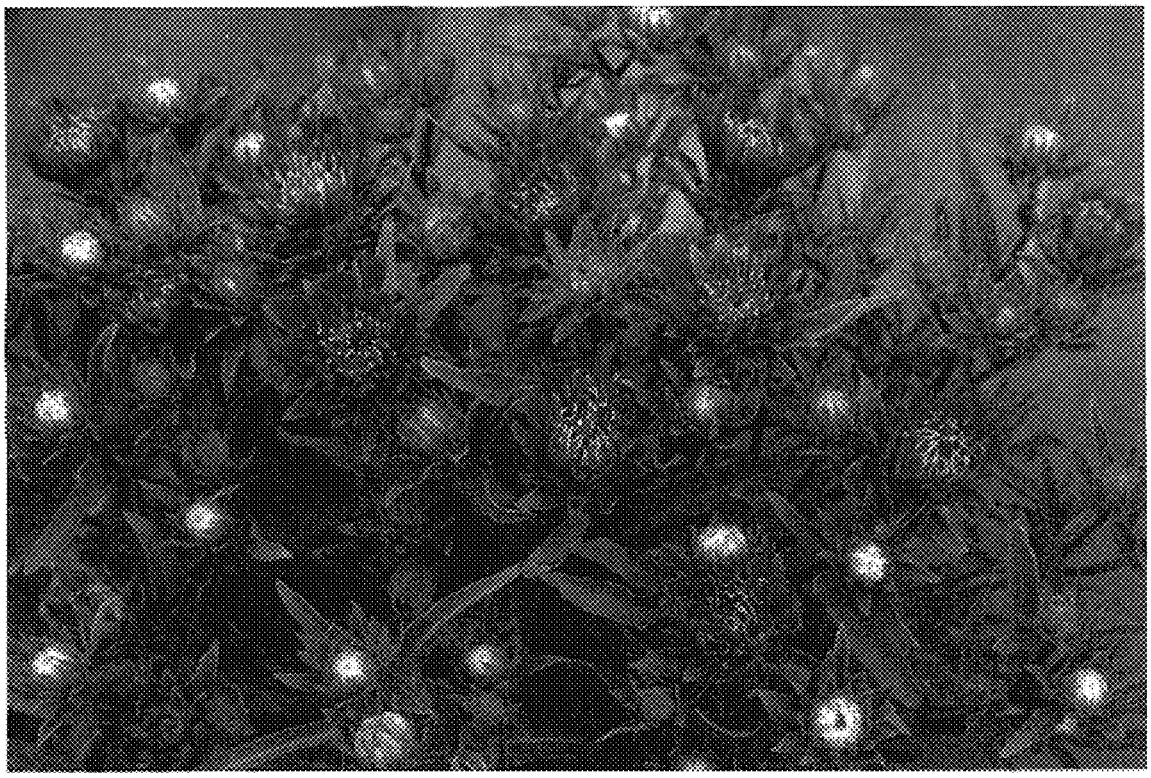

* * * * *